(12) United States Patent
Cheng

(10) Patent No.: US 9,684,003 B2
(45) Date of Patent: Jun. 20, 2017

(54) DETECTION DEVICE, DETECTION KIT, AND DETECTION METHOD

(71) Applicant: NATIONAL TSING HUA UNIVERSITY, Hsinchu (TW)

(72) Inventor: Chao-Min Cheng, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 15/244,468

(22) Filed: Aug. 23, 2016

(65) Prior Publication Data

US 2017/0122967 A1    May 4, 2017

(30) Foreign Application Priority Data

Oct. 28, 2015 (TW) .............................. 104135325 A

(51) Int. Cl.
  *G01N 33/558* (2006.01)
  *G01N 33/80* (2006.01)
  *G01N 33/538* (2006.01)

(52) U.S. Cl.
  CPC ........... *G01N 33/80* (2013.01); *G01N 33/538* (2013.01)

(58) Field of Classification Search
  None
  See application file for complete search history.

(56) References Cited

U.S. PATENT DOCUMENTS 1,944,926 A * 1/1934 Colbeth ............. G01N 33/2805
                                            422/401
4,225,575 A * 9/1980 Piasio ..................... C12Q 1/00
                                            422/417
5,073,484 A * 12/1991 Swanson ............. G01N 33/558
                                            422/424
2003/0054567 A1   3/2003  Miyoshi et al.
2009/0187350 A1   7/2009  Chau et al.
2010/0098587 A1   4/2010  Miyoshi et al.
2010/0098591 A1   4/2010  Miyoshi et al.
2010/0099179 A1   4/2010  Miyoshi et al.
2010/0104475 A1   4/2010  Miyoshi et al.
2013/0022960 A1   1/2013  Xu et al.

FOREIGN PATENT DOCUMENTS

| CN | 86203547   U | 8/1987  |
| CN | 1373365    A | 10/2002 |
| CN | 1529149    A | 9/2004  |
| TW | 200935042  A | 8/2009  |

\* cited by examiner

*Primary Examiner* — Chris L Chin
(74) *Attorney, Agent, or Firm* — Muncy, Geissler, Olds & Lowe, P.C.

(57) ABSTRACT

Disclosed is a detection method, including steps of: providing an elongated carrier with a plurality of recognition substances fixed thereon; bringing a first end of the elongated carrier in contact with a liquid sample to permit the liquid sample to move towards an opposite second end along the elongated carrier, therewith a plurality of coloring elements in the liquid sample forming a colored band on the elongated carrier; and determining whether the liquid sample contains analytes based on the length of the colored band. Accordingly, the analytes can be detected by recognizing the agglutination based on the length of the colored band. Additionally, the present invention also provides a detection device and a detection kit for the aforementioned detection process.

19 Claims, 4 Drawing Sheets

DETECTION DEVICE, DETECTION KIT, AND DETECTION METHOD

CROSS REFERENCE TO RELATED APPLICATION

This application claims the benefits of the Taiwan Patent Application Serial Number 104135325, filed on Oct. 28, 2015, the subject matter of which is incorporated herein by reference.

BACKGROUND OF THE INVENTION

1. Field of the Invention

The present invention relates to a detection device, a detection kit, and a detection method, more particularly, to a detection device, a detection kit, and a detection method applying an agglutination reaction.

2. Description of Related Art

Hemagglutination test is a common test for blood type identification or virus detection based on the hemagglutination phenomena caused by lectin, antibodies, or virus. For example, blood cell grouping test and serum grouping test may be performed according to agglutination reactions, wherein the blood cell grouping test may be performed utilizing antibody A and antibody B for blood type identification. That is, the blood type A may be determined by the blood cell grouping test if the blood agglutinates against antibody A and fails to agglutinate against antibody B; whereas the blood type B may be determined by the serum grouping test if the plasma or serum agglutinates against erythrocytes with antigen A but fails to agglutinates against erythrocytes with antigen B. Furthermore, the virus causing the agglutination reaction may also be detected based on the agglutination reaction.

Currently, the agglutination reaction test is performed by plate agglutination test and tube agglutination test, however, the individual errors of interpretation of the test results may easily occur, and the requirements of simplification and standardization cannot be achieved due to the cumbersome operational procedures. Accordingly, it is desirable to provide a novel detection technique which is advantageous for simple operation, easy interpretation, and rapid detection.

SUMMARY OF THE INVENTION

An object of the present invention is to provide a simple detection method in which agglutination of a tested sample can be interpreted quickly and directly by the naked eyes without the assistance of any physical or chemical auxiliary equipment. The detection method is suitable for instant detection with less individual interpretation error.

To achieve the object, the detection method of the present invention includes the steps of: providing an elongated carrier with a plurality of recognizing substances fixed thereon, wherein the elongated carrier has a first end and an opposite second end; bringing the first end of the elongated carrier in contact with the a liquid sample and allowing the liquid sample to move toward the second end along the elongated carrier, therewith a colored band extending from the first end toward the second end is formed on the elongated carrier by a plurality of coloring elements in the liquid sample; and determining whether the liquid sample contains a plurality of analytes by distinguishing whether the colored band is an agglutination colored band or an expanded colored band based on the length of the colored band. When the liquid sample contains the analytes, the recognizing substances are able to bind to the analytes so that the coloring elements form the agglutination colored band, wherein a length of the agglutination colored band is shorter than a length of the expanded colored band in the absence of the analytes.

Accordingly, the user may dip a small amount of the liquid sample at one end of the elongated carrier for determining whether the liquid sample contains the analytes based on the length of the colored band that formed on the elongated carrier. The detection method of the present invention is simple and can rapidly detect the analytes. The detection method is applicable for those detection methods determining the existent of an analyte by interpreting whether an agglutination reaction occurs, that is, the detection method of the present invention is applicable for detecting those analytes that are able to induce the agglutination reaction of the coloring elements. For example, the detection method of the present invention may be applied for identification of blood type using the erythrocytes in the blood sample as the coloring elements, and the antibody A or the antibody B as the recognizing substances for detecting whether the analytes comprising antibody A or antibody B exist in the blood sample. If the blood type of the blood sample is blood type A or AB, a red agglutination colored band will be formed at the front end of the elongated carrier containing antibody A by the agglutination of the erythrocytes; if the blood type of the blood sample is blood type B or O, a red expanded colored band will be formed by the erythrocytes distributed uniformly on the elongated carrier. In the case that the antibody B is used as the recognizing substances, a red agglutination colored band will be formed at the front end of the elongated carrier containing antibody B by the agglutination of the erythrocytes if the blood type of the blood sample is blood type B or AB; whereas a red expanded colored band will be formed by the erythrocytes uniformly distributed on the elongated carrier if the blood type of the blood sample is blood type A or O. For the convenience of comparing the length of the agglutination colored band and the expanded colored band, the elongated carrier can have a spiral segment with a plurality of loops being formed along a central axis. Accordingly, the expanded colored band or the agglutination colored band that extends on the elongated carrier is formed by the coloring elements when the liquid sample moves from the first end of the elongated carrier toward the second end and reaches the spiral segment. For example, a single spiral band having a plurality of colored loops is formed when the liquid sample does not contain those analytes. On the contrary, the agglutination colored band will not extend to the spiral segment (with no colored loops formed) or the agglutination colored band having less colored loops than that of the expanded colored band is formed when the liquid sample contains the analytes. Therefore, the existence of the analyte in the liquid sample may be determined by the number of the colored loops formed on the spiral segment.

According to the aforementioned detection method, the present invention further provides a detection device, which comprises an elongated carrier having a spiral segment with a plurality of loops along a central axis, and having a first end and an opposite second end. The elongated carrier allows a liquid sample to move from the first end toward the second end and reach the spiral segment after the first end contacts with the liquid sample, wherein an agglutination colored band or an expanded colored band extending from the first end toward the second end of the elongated carrier is formed by a plurality of coloring elements in the liquid sample. The detection device further comprises a plurality of recognizing substances being fixed on the elongated carrier. The recognizing substances are able to bind to a plurality of analytes in the liquid sample so that the coloring elements form the agglutination colored band, wherein a length of the agglutination colored band is shorter than a length of the expanded colored band in the absence of the analytes.

In addition, the present invention also provides a detection kit, which comprises an elongated carrier having a spiral segment with a plurality of loops along a central axis, and having a first end and an opposite second end. The elongated carrier allows a liquid sample to move from the first end toward the second end and reach the spiral segment after the first end contacts with the liquid sample, wherein an agglutination colored band or an expanded colored band extending from the first end toward the second end of the elongated carrier is formed by a plurality of coloring elements in the liquid sample. The detection kit further includes a coating solution comprising a plurality of recognizing substances and a solvent, wherein the recognizing substances are fixed on the elongated carrier. The recognizing substances are able to bind to a plurality of analytes in the liquid sample so that the coloring elements form the agglutination colored band, wherein a length of the agglutination colored band is shorter than a length of the expanded colored band which is in the absence of the recognizing substances.

In the present invention, the elongated carrier is not particularly limited as long as the liquid sample can move from the first end toward the second end of the elongated carrier, and the recognizing substances can be fixed thereon for forming the expanded colored band or the agglutination colored band as the liquid sample moves within the elongated carrier. For example, the elongated carrier may comprise a fibrous material, so that the recognizing substances may be fixed on the fibrous materials by adhesive. Accordingly, the liquid sample may move along a longitude direction of the elongated carrier by capillary action and the coloring elements may form a colored band on the fibrous material simultaneously. Furthermore, the elongated carrier may be formed with a single-layered or a multi-layered elongated configuration, and a spiral segment thereof may be formed by any winding method. For example, the elongated carrier may be a cotton thread wherein the spiral segment may be formed by winding and fixing the cotton thread on a central rod; alternatively, the elongated carrier may include a flexible core and a fibrous layer covering the flexible core wherein the spiral segment may be formed by the flexible feature of the flexible core.

In the present invention, the recognizing substances are not particularly limited as long as the recognizing substances are able to bind with the analytes, and are preferably able to specifically bind with the analytes, such as antigens, proteins, and other biomolecules, which are not limited thereto. In addition, the method for fixing the recognizing substance on the elongated carrier is not particularly limited, which can be any physical or chemical methods such as adsorption or covalent bonding. However, the recognizing substances are preferably fixed on the elongated carrier by adsorption considering the cost and simple operation, for example, antibody A/antibody B for recognizing antigen A/antigen B is fixed on the cotton thread by adsorption in an embodiment of the present invention.

In the present invention, the detection device/kit may further comprise a housing having an inlet with an inner space formed inside the housing, wherein the elongated carrier is disposed in the inner space with the first end of the elongated carrier facing toward the inlet, so that the liquid sample entering the inner space through the inlet is directed to the first end of the elongated carrier. The housing herein may be a transparent housing which is beneficial for the user to observe the length of the colored band directly.

In the present invention, the detection device/kit may further comprise a rod having a front end and an opposite rear end, wherein the rod is disposed in the inner space through an opening of the housing opposite to the inlet so that the rod is slidably disposed in the inner space and tightly fits to a sidewall of the housing with the rear end of the rod protruding out of the housing through the opening for applying a drawing process performed by a user. Accordingly, the front end of the rod can move between the second end of the elongated carrier and the opening of the housing for drawing the coating solution so that the whole elongated carrier or a portion of the elongated carrier may be immersed in the coating solution for fixing the recognizing substances on the elongated carrier. Alternatively, the rod can be used for drawing the liquid sample so that the first end of the elongated carrier may be immersed in the liquid sample for the detection.

In the present invention, the detection device/kit may further comprise a needle body which is engagingly disposed at the inlet of the housing so that the liquid sample may be directed into the inner space of the housing therethrough. Accordingly, the needle body may be utilized for drawing the liquid sample directly from the subjects. For example, the needle body may be utilized to draw blood directly from a patient's blood vessels for the subsequent detection process.

In summary, the present invention provides a detection device/kit with low cost and simple operation that may be used to detect an analyte rapidly. Particularly, the individual errors of interpretation of the test results may be reduced by determining whether the agglutination occurs with the length of the colored band. Moreover, the present invention may be widely applied to any detection process for detecting an analyte based on the agglutination phenomena, for example, the analytes of the present invention may be, but not limited to, antibody A or antibody B of erythrocytes, C-reactive protein (CRP), or hemagglutination proteins of the virus.

DETAILED DESCRIPTION OF THE PREFERRED EMBODIMENT

The following specific examples will be provided for implementing the technical feature of the present invention. The advantages and effects of the present invention may easily understand by those skilled in the art referring the description of the present specification. It is to be understood that many other possible modifications and variations can be made without departing from the spirit and scope of the invention as hereinafter claimed.

[Embodiment 1]

Figure 1:
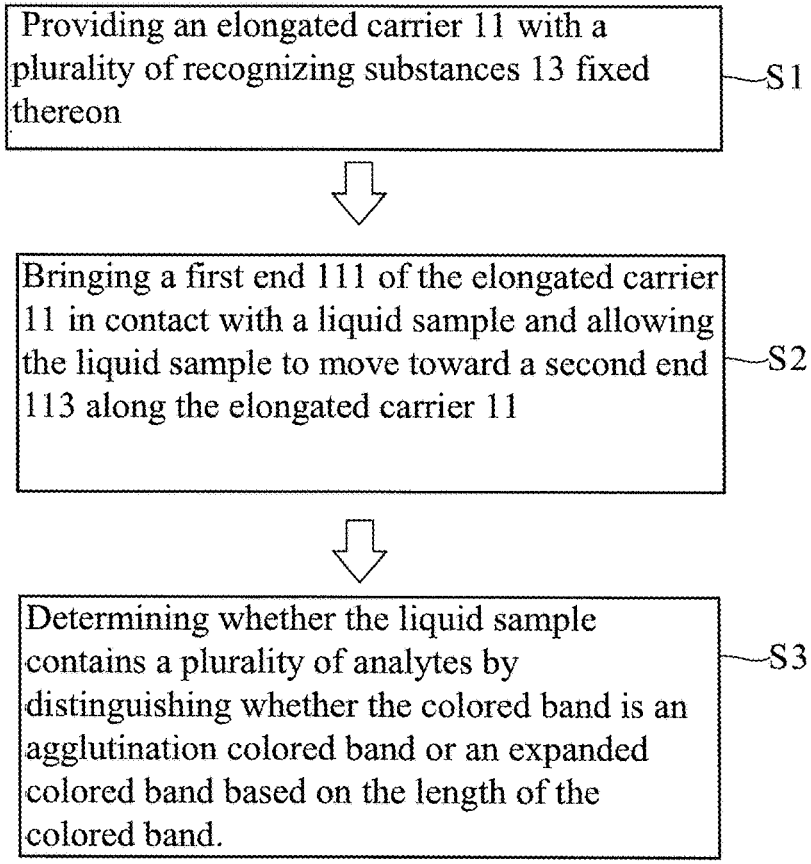
FIG. 1 is a flowchart of the detection method of an embodiment of the present invention.

FIG. 1 shows a flowchart of the detection method of an embodiment of the present invention. The detection result of the detection method of the present invention is interpreted based on the length differences between the colored bands, therefore, the detection method of the present invention may be applied to any detection process for detecting an analyte based on the agglutination phenomena, such as the detection of blood type, c-reactive protein (CRP), or virus, etc. The detection method will be described as follows with reference to the detection device 100 illustrated in FIG. 2.

Step S1: providing an elongated carrier 11 with a plurality of recognizing substances 13 fixed thereon. The present embodiment utilized a cotton thread (nitrocellulose) as the elongated carrier 11. The elongated carrier 11 was immersed in a coating solution comprising a plurality of recognizing substances 13 for adsorbing the recognizing substances; the elongated carrier 11 was then dried at room temperature so that the recognizing substances 13 were completely coated on the surface of the thread. Hereinafter, the antibody A or antibody B for identifying blood type is used as the recognizing substances 13 of the present embodiment.

Figure 2:
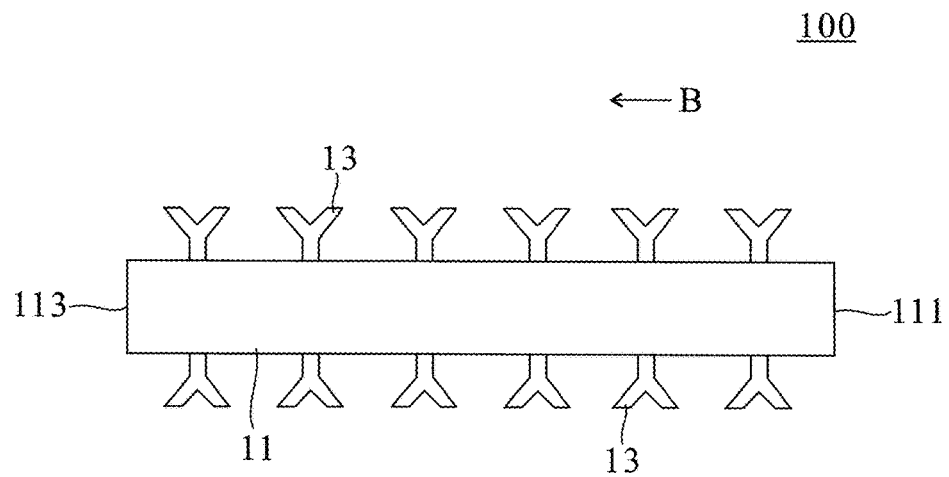
FIG. 2 is a schematic view of the detection device of an embodiment of the present invention.

Step S2: bringing a first end 111 of the elongated carrier 11 in contact with a liquid sample and allowing the liquid sample to move toward a second end 113 along the elongated carrier 11 (as indicated by arrow B in FIG. 2). A colored band (not shown) extending from the first end 111 toward the second end 113 is formed on the elongated carrier 11 by a plurality of coloring elements (not shown) in the liquid sample. First, one end of the elongated carrier 11 coated with the recognizing substances 13 is dipped with a small amount of blood, the blood sample was directed toward another end of the elongated carrier 11 by capillary action, and a red colored band was formed simultaneously on the thread with erythrocytes in the blood sample.

Figure 3:
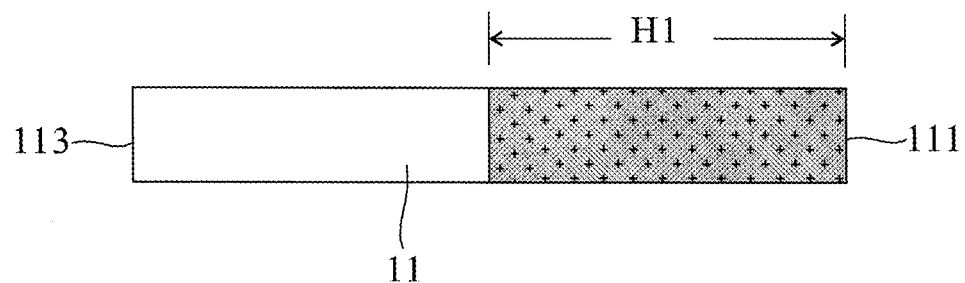
FIG. 3 and FIG. 4 are schematic views of the test results of an embodiment of the present invention.
Figure 4:
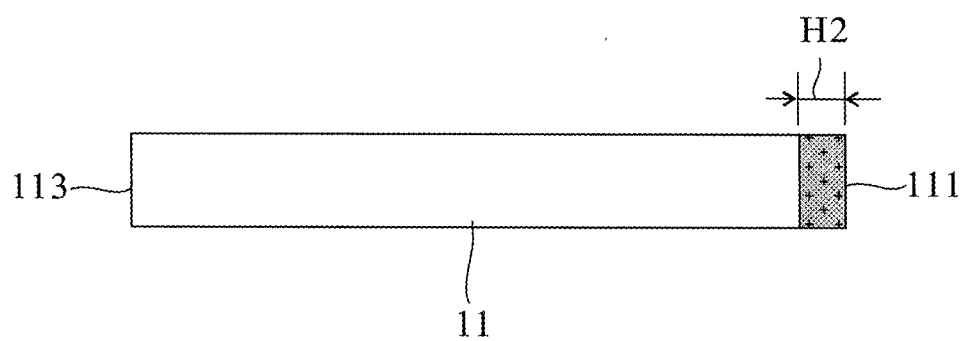

Step S3: determining whether the liquid sample contains a plurality of analytes by distinguishing whether the colored band is an agglutination colored band or an expanded colored band based on the length of the colored band. Please refer to FIG. 3, which shows the detection result of the blood sample without the analyte using the detection device 100. Accordingly, the expanded colored band H1 is formed on the elongated carrier 11 by erythrocytes when the blood sample is in the absence of analytes. On the contrary, FIG. 4 shows the detection result of the blood sample including the analytes using the detection device 100. An agglutination colored band H2 is formed by the erythrocytes of the blood sample agglutinating at the front end of the elongated carrier 11 when the blood sample contains the analytes. The length of the agglutination colored band H2 is apparently shorter than that of the expanded colored band H1 in the absence of the analyte. Hereinafter, the analytes are antigen A when the detection device 100 utilizes antibody A as the recognizing substances; whereas the analytes are antigen B when antibody B is utilized as the recognizing substances.

More specifically, when the detection is performed with the thread coated with antibody A, the antigen A contained in erythrocytes of blood type A or AB will bind to the antibody A on the thread, therefore, the erythrocytes will agglutinate at the front end of the thread if the blood sample is of blood type A or AB. Correspondingly, the erythrocytes will expand uniformly by the capillary action on the thread if the blood sample is of blood type B or O. In addition, when the detection is performed with the thread coated with antibody B, the erythrocytes of blood type B or AB will agglutinate at the front end of the thread; on the contrary, the erythrocyte of blood type A or O will expand uniformly by the capillary action on the thread. Accordingly, if an agglutination colored band is formed on the thread coated with antibody A and an expanded colored band is formed on another thread coated with antibody B, the blood sample will be determined as blood type A; if an expanded colored band is formed on the thread coated with antibody A and an agglutination colored band is formed on another thread coated with antibody B, the blood sample will be determined as blood type B; if agglutination colored bands are formed on both the threads coated with antibody A and antibody B, the blood sample will be determined as blood type AB; and if expanded colored bands are formed on both the threads coated with antibody A and antibody B, the blood sample will be determined as blood type O.

Based on the aforementioned description, the present embodiment utilizes antibody A and antibody B as recognizing substances, and utilizes erythrocytes as the coloring elements. The existence of antigen A or antigen B in the blood sample may be determined based on the length of the colored band on the thread formed by erythrocytes. That is, the existence of certain analytes in a liquid sample will be confirmed if an agglutination colored band (shorter and concentrated colored band) is formed on the elongated carrier. On the contrary, the absence of certain analytes in a liquid sample will be confirmed if an expanded colored band (longer and dispersed colored band) is formed on the elongated earner.

Figure 5:
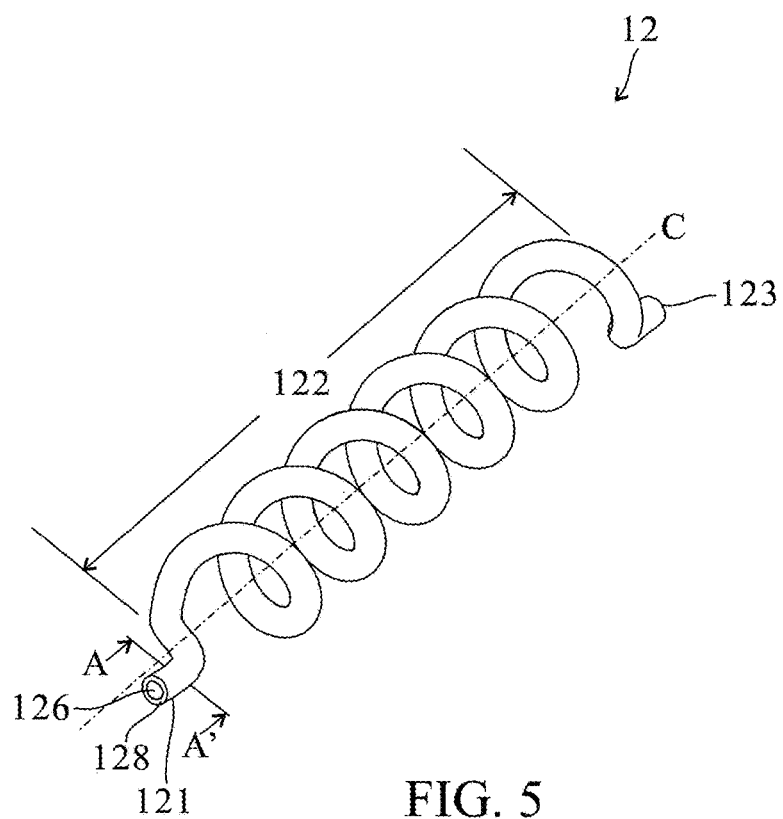
FIG. 5 is a perspective view of the elongated carrier of an embodiment of the present invention.
Figure 6:
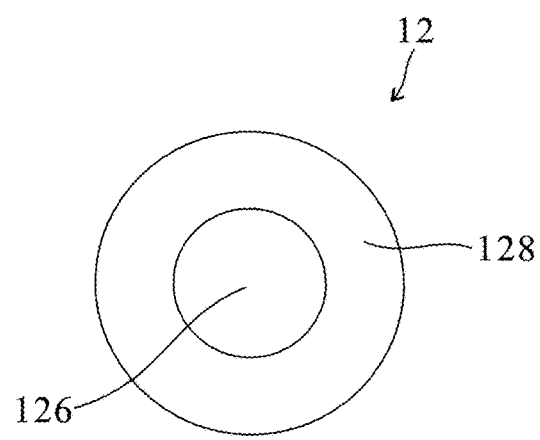
FIG. 6 is a cross-sectional view along the line A-A' in FIG. 5.

In addition, refer to FIG. 5 and FIG. 6 which illustrate the perspective view and the cross-sectional view of the elongated carrier respectively. As illustrated in FIG. 5 and FIG. 6, the elongated carrier 12 comprises a flexible core 126 and a fibrous layer 128 covering the flexible core 126. The present embodiment utilized copper wire as the flexible core 126, and nitrocellulose layer was utilized as the fibrous layer 128 to cover the copper wire. Accordingly, a spiral segment 122 with a plurality of loops of the elongated carrier 12 may be formed corresponding to the central axis C due to the flexible property of the flexible core 126, and the fibrous layer 128 allows the liquid sample to move from a first end 121 toward a second end 123 by capillary action.

As described above, the recognizing substances (not shown) may be fixed on the fibrous layer 128 for the detection process illustrated in FIG. 1. Accordingly, more colored loops may be observed at the spiral segment 122 when an expanded colored band is formed on the fibrous layer 128 of the elongated carrier 12 so as to learn that the liquid sample does not contain the analyte. On the other hand, less colored loops may be observed at the spiral segment when an agglutination colored band is formed so as to learn that the liquid sample contains the analyte. Therefore, the existence of the analyte in a liquid sample may be determined directly by observing the number of the colored loops of the spiral segment 122 using the elongated carrier 12 of the present embodiment.

In practical applications, the elongated carrier with recognizing substances fixed thereon may be used directly as the detection device, or a detection kit comprising an elongated carrier and a coating solution comprising a plurality of recognizing substances and a solvent may be provided for the users to fix the recognizing substances on the elongated carrier before conducting the detection process.

[Embodiment 2]

Figure 7:
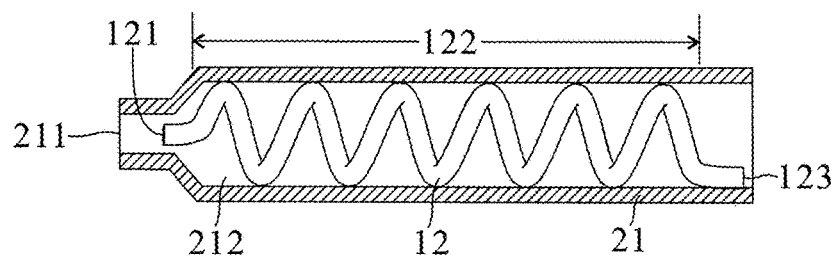
FIG. 7 is a lateral view of the detection device of another embodiment of the present invention.

Please refer to FIG. 7, which illustrate a lateral view of a detecting device 200 of another embodiment. As illustrated in FIG. 7, the elongated carrier 12 of FIG. 5 was applied in the present embodiment, and the elongated carrier 12 with the recognizing substances (not shown) fixed thereon was disposed in a housing 21 for forming the detection device 200. The housing 21 has an inlet 211 with an inner space 212 formed inside the housing 21, wherein the elongated carrier 12 is disposed in the inner space 212 with the first end 121 of the elongated carrier 12 facing toward the inlet 211, so that the liquid sample may enter the inner space 212 through the inlet 211. The liquid sample entering the inner space 212 may infiltrate the first end 121 of the elongated carrier 12, and move toward the second end 123 by capillary action for forming a colored band extending to the spiral segment 122. The housing 21 used herein is a transparent housing which is beneficial for the user to observe the number of the colored loops directly. In addition, the present embodiment may be applied to a detection kit described in embodiment 1, wherein a coating solution comprising a plurality of recognizing substances is provided for the users to fix the recognizing substances on the elongated carrier before the conducting detection process.

[Embodiment 3]

Figure 8:
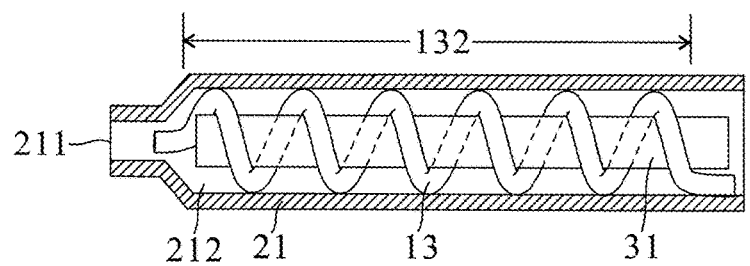
FIG. 8 is a lateral view of the detection device of another embodiment of the present invention.

The lateral view of the detection device 300 of another embodiment of the present invention is illustrated in FIG. 8. According to FIG. 8, the detection device 300 of the present embodiment is similar to that of Embodiment 2 except that a thread is utilized as the elongated carrier 13 in the present embodiment, and the spiral segment is formed by winding the elongated carrier 13, which is disposed in the inner space 212, on a central rod 31. Similarly, the present embodiment may be applied to a detection kit, wherein a coating solution comprising a plurality of recognizing substances is provided for the users to fix the recognizing substances on the elongated carrier before conducting the detection process.

[Embodiment 4]

Figure 9:
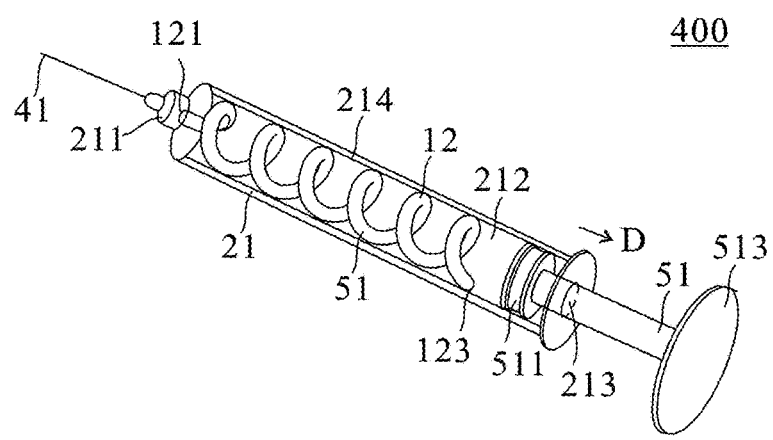
FIG. 9 is a perspective view of the detection device of another embodiment of the present invention.

The perspective view of the detection device 400 of another embodiment of the present invention is illustrated in FIG. 9. According to FIG. 9, the detection device 400 is similar to that of Embodiment 2, except that the detection device 400 further comprises a needle body 41 and a rod 51. The needle body 41 is engagingly disposed at the inlet 211 of the housing 21, and the rod 51 is embedded in the inner space 212 through the opening 213 of the housing 21 so that the front end 511 of the rod 51 is able to be slidably disposed in the inner space 212 and tightly fit to the sidewall 214 of the housing 21 with the rear end 513 of the rod 51 protruding out of the housing 21 through the opening 213. Accordingly, the needle body 41 may be applied for drawing a liquid sample from a subject, and the liquid sample could be directed into the inner space 212 through the needle body 41 to infiltrate the first end 121 of the elongated carrier 12. For example, the needle body 41 may be applied directly inserted to draw blood from a patient's blood vessels by pulling the rear end 513 of the rod 51 along the direction of the arrow D. Similarly, when a detection kit is applied, the rod 51 may be used for drawing the coating solution so that the elongated carrier 21 may be immersed in the coating solution, and the recognizing substances may be fixed on the elongated carrier 21.

Although the present invention has been explained in relation to its preferred embodiment, it is to be understood that many other possible modifications and variations can be made without departing from the spirit and scope of the invention as hereinafter claimed.

What is claimed is:

1. A detection device, comprising:
an elongated carrier having a spiral segment with a plurality of loops along a central axis, and having a first end and an opposite second end, wherein the elongated carrier allows a liquid sample to move from the first end toward the second end and reach the spiral segment after the first end contacts with the liquid sample, wherein an agglutination colored band or an expanded colored band extending from the first end toward the second end of the elongated carrier is formed by a plurality of coloring elements in the liquid sample; and
a plurality of recognizing substances being fixed on the elongated carrier, the recognizing substances being able to bind to a plurality of analytes in the liquid sample so that the coloring elements form the agglutination colored band, wherein a length of the agglutination colored band is shorter than a length of the expanded colored band in absence of the analytes.

2. The detection device as claimed in claim 1, wherein the elongated carrier comprises a fibrous material.

3. The detection device as claimed in claim 1, wherein the liquid sample moves toward the second end by capillary action.

4. The detection device as claimed in claim 1 to claim 3, further comprising a housing having an inlet and forming an inner space, wherein the elongated carrier is disposed in the inner space with the first end of the elongated carrier facing toward the inlet, so that the liquid sample entering the inner space through the inlet is directed to the first end of the elongated carrier.

5. The detection device as claimed in claim 4, further comprising a rod having a front end and an opposite rear end, wherein the rod is disposed in the inner space through an opening of the housing opposite to the inlet so that the rod is slidably disposed in the inner space and tightly fits to a sidewall of the housing with the rear end of the rod protruding out of the housing through the opening for applying a drawing process performed by a user.

6. The detection device as claimed in claim 5, further comprising a needle body engagingly disposed at the inlet of the housing so as to direct the liquid sample into the inner space therethrough.

7. A detection kit, comprising:
an elongated carrier having a spiral segment with a plurality of loops along a central axis, and having a first end and an opposite second end, wherein the elongated carrier allows a liquid sample to move from the first end toward the second end and reach the spiral segment after the first end contacts with the liquid sample, wherein an agglutination colored band or an expanded colored band extending from the first end toward the second end of the elongated carrier is formed by a plurality of coloring elements in the liquid sample; and
a coating solution comprising a plurality of recognizing substances and a solvent, wherein the recognizing substances are fixed on the elongated carrier, the recognizing substances being able to bind to a plurality of analytes in the liquid sample so that the coloring elements form the agglutination colored band, wherein a length of the agglutination colored band is shorter than a length of the expanded colored band in absence of the analytes.

8. The detection kit as claimed in claim 7, wherein the elongated carrier is made of fibrous material.

9. The detection kit as claimed in claim 7, wherein the liquid sample moves toward the second end by capillary action.

10. The detection kit as claimed in claim 7 to claim 9, further comprising a housing having an inlet and forming an inner space, wherein the elongated carrier is disposed in the inner space with the first end of the elongated carrier facing toward the inlet, so that the liquid sample entering the inner space through the inlet is directed to the first end of the elongated carrier.

11. The detection kit as claimed in claim 10, further comprising a rod having a front end and an opposite rear end, wherein the rod is disposed in the inner space through an opening of the housing opposite to the inlet so that the rod is slidably disposed in the inner space and tightly fits to a sidewall of the housing with the rear end of the rod protruding out of the housing through the opening for applying a drawing process performed by a user.

12. The detection kit as claimed in claim 11, further comprising a needle body engagingly disposed at the inlet of the housing so as to direct the liquid sample into the inner space therethrough.

13. A method for detection of a plurality of analytes in a liquid sample, comprising steps of:
providing an elongated carrier with a plurality of recognizing substances fixed thereon, wherein the elongated carrier has a first end and an opposite second end and a spiral segment with a plurality of loops along a central axis;
bringing the first end of the elongated carrier in contact with a liquid sample and allowing the liquid sample to move toward the second end along the elongated carrier and reach the spiral segment, therewith a colored band extending from the first end to the second end is formed on the elongated carrier by a plurality of coloring elements in the liquid sample; and
determining whether the liquid sample contains a plurality of analytes by distinguishing whether the colored band is an agglutination colored band or an expanded colored band based on the length of the colored band;
wherein when the liquid sample contains the analytes, the recognizing substances are able to bind to the analytes so that the coloring elements form the agglutination colored band, wherein a length of the agglutination colored band is shorter than a length of the expanded colored band in the absence of the analytes.

14. The method as claimed in claim 13, wherein the elongated carrier comprises a fibrous material.

15. The method as claimed in claim 13, wherein the liquid moves toward the second end by capillary action.

16. The method as claimed in claim 13, wherein the detection method determines whether the analyte is contained in the liquid sample according to the number of the loops being colored by the liquid sample.

17. The method as claimed in claim 13, wherein the detections method is performed by a detection unit as claimed in any one of claim 4 to claim 6.

18. The method as claimed in any one of claim 13 to claim 17, wherein the detection method is applied for identification of blood types.

19. The method as claimed in claims 18, wherein the recognizing substances are antibody A or antibody B, the analytes are antigen A or antigen B, and the coloring elements are erythrocytes.

\* \* \* \* \*